US00PP31069P3

(12) United States Plant Patent
Meilland

(10) Patent No.: US PP31,069 P3
(45) Date of Patent: Nov. 19, 2019

(54) BEDDING ROSE PLANT NAMED 'MEICERAFYN'

(50) Latin Name: *Rosa hybrida*
Varietal Denomination: MEICERAFYN

(71) Applicant: THE CONARD-PYLE COMPANY, West Grove, PA (US)

(72) Inventor: Alain A. Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,711

(22) Filed: Apr. 12, 2018

(65) Prior Publication Data

US 2019/0320567 P1 Oct. 17, 2019

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./102, 107, 108, 130, 137, 138, 139, Plt./140, 141, 148, 149, 150, 151
CPC ..... A01H 5/0222; A01H 5/02; A01H 5/00; A01H 5/0216; A01H 6/749; A01H 6/74
See application file for complete search history.

(56) References Cited

PUBLICATIONS

Monrovia 2019 Grace N' Grit Pink Shrub Rose, retrieved on Mar. 20, 2019, retrieved from the Internet at https://www.monrovia.com/plant-catalog/plants/6233/grace-n-grit-pink-shrub-rose/, 2 pp. (Year: 2019).*

Monrovia Releases Record Breaking Number of New Plants in 2018, retrieved on Mar. 19, 2019, retrieved from the Internet at https://www.globenewswire.com/news-release/2017/11/01/1172660/0/en/Monrovia-Releases-Record-Breaking-Number-of-New-Plants-in-2018.html, 2 pp. (Year: 2017).*

* cited by examiner

*Primary Examiner* — June Hwu
(74) *Attorney, Agent, or Firm* — Buchanan Ingersoll & Rooney PC

(57) ABSTRACT

A new and distinct variety of Bedding Rose plant, herein referred to by its cultivar name, 'MEICERAFYN', is provided which forms very abundantly on a nearly continuous basis attractive, cup-shaped, red-purple colored blossoms. Attractive, glossy, very dense foliage is formed, which contrasts beautifully with the blossoms. A compact, bushy growth habit is displayed. The disease tolerance is exceptional, particularly against rust and Black Spot. The new variety is well suited for proving attractive ornamentation in the landscape and is very floriferous.

1 Drawing Sheet

Figures 1, 2, 3, 4, 5, 6, 7, 8, 9, 10, 11, 12, 13, 14, 15:
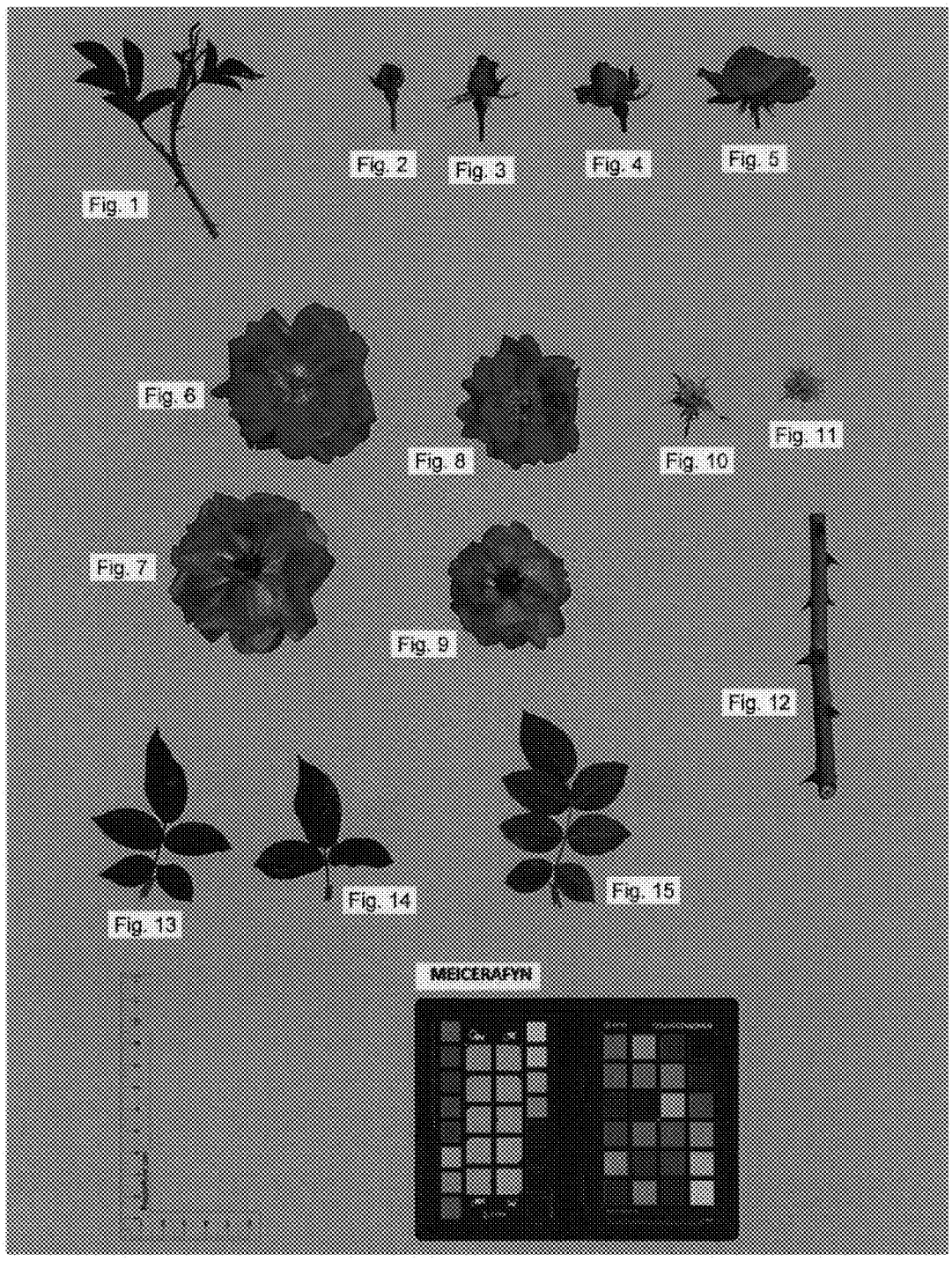

Botanical/commercial classification:
Latin name—*Rosa hybrida.*
Common name—Bedding Rose Plant.
Varietal denomination: 'MEICERAFYN'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the 'NOAWEL' variety (non-patented in the United States). The male parent (i.e., the pollen parent) was the 'RADRAZZ' variety (U.S. Plant Pat. No. 11,836).

The parentage of the new variety can be summarized as follows:

'NOAWEL' x 'RADRAZZ'

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) very abundantly and nearly continuously forms attractive, cup-shaped, red-purple colored blossoms,
(b) forms attractive, very dense, glossy foliage,
(c) exhibits exceptional tolerance to diseases, particularly against rust and Black Spot,
(d) is very floriferous,
(e) exhibits a compact, bushy growth habit, and
(f) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'NOAWEL' variety (i.e., the seed parent) displays a darker coloration of blossoms than that of the new variety. The 'RADRAZZ' variety (i.e., the pollen parent) exhibits less resistance to rust than the new variety. Moreover, the new variety can be readily distinguished from non-parental related similar varieties. For example, the 'Meimacota' variety (U.S. Plant Pat. No. 30,537) displays larger flowers compared to the new variety.

The new variety has been found to undergo asexual propagation in Le Cannet des Maures, France by a number of routes, including budding, eye budding grafting, and the use of softwood, hardwood, and semi-hardwood cuttings. Asexual propagation by the above-mentioned techniques in Le Cannet des Maures, France has shown that the characteristics of the new variety are stable and are strictly transmissible by such asexual propagation from one generation to another. Accordingly, the new variety undergoes asexual propagation in a true-to-type manner.

The new variety has been named 'MEICERAFYN'.

BRIEF DESCRIPTION OF THE PHOTOGRAPH

The accompanying photographs show as nearly true as it is reasonably possible to make the same, in a color illustration of this character, typical specimens of the plant parts of the new variety. The rose plants of the new variety were approximately two years of age and were observed during July while budded on their own roots and growing outdoors at Le Cannet des Maures, Var, France. Standard color information and dimensions in centimeters are included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening of the petals.

FIG. 5—illustrates a specimen of a flower in the course of opening.

FIG. 6—illustrates a specimen of a fully open flower—plan view—obverse.

FIG. 7—illustrates a specimen of a fully open flower—plan view—reverse.

FIG. 8—illustrates a specimen of a flower in the course of opening—plan view—obverse.

FIG. 9—illustrates a specimen of a flower in the course of opening—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 5 leaflets—plan view—upper surface.

FIG. 14—illustrates a specimen of a leaf with 3 leaflets—plan view—upper surface.

FIG. 15—illustrates a specimen of a leaf with 7 leaflets—plan view—under surface.

DETAILED BOTANICAL DESCRIPTION

The chart used in the identification of the colors is that of The Royal Horticultural Society (R.H.S. Color Chart, edition 2001), London, England. The terminology which precedes reference to the chart has been added to indicate the corresponding color in more common terms. The description is based on the observation of two-year-old specimens of the new variety during July while budded on their own roots and growing outdoors at Le Cannet des Maures, Var, France.

Class: Bedding Rose Plant.

Plant:

*Habit*.—Compact, bushy.

*Height*.—Approximately 52.5 cm on average.

*Spread*.—Approximately 66 cm on average.

Branches:

*Color*.—Young stems: commonly near Yellow-Green Group 146B; intensity of anthocyanin coloration is low to medium. Adult wood: commonly near Yellow-Green Group 146A.

*Thorns*.—Configuration on adult stems: curved downward on the upper surface and concave on the under surface. Long prickles — quantity: commonly approximately 7 thorns per 10 cm long young stem and commonly 9 thorns per 10 cm long adult stem. Long prickles — base shape: oval. Long prickles — size: commonly near 0.9 cm in length on average on young stems and commonly near 1.1 cm in length on average on adult stems. Long prickles — color: commonly near Greyed-Orange Group 164B on young stems and commonly near Greyed-Orange Group 166B on adult stems. Small prickles (<0.8 cm): none observed.

Foliage:

*General appearance*.—Very dense with a glossy aspect.

*Number of leaflets*.—3, 5, and 7; most often 7.

7 *leaflet leaf*.—Length: approximately 12 cm on average. Width: approximately 9 cm on average. Terminal leaflet length: approximately 5.6 cm on average. Width: approximately 3.0 cm on average.

*Glossiness intensity of the upper surface of the leaf*.—Strong.

*New foliage*.—Upper surface color: commonly near Green Group 137B more or less suffused with Greyed-Purple Group 183A. Under surface color: commonly near Green Group 137C more or less suffused with Greyed-Purple Group 183A.

*Adult foliage*.—Upper surface color: commonly near Yellow-Green Group 147A. Under surface color: commonly near Yellow-Green Group 147B.

Leaflets:

*Shape*.—Tip: acuminate. Base: obtuse.

*Texture*.—Leathery.

*General appearance*.—Oval.

*Edge*.—Slightly denticulate.

*Serration*.—Small and single.

*Petiole rachis*.—Color of upper surface: commonly near Yellow-Green Group 146D. Color of under surface: commonly near Yellow-Green Group 146B.

*Petioles*.—Upper surface: no glandular. Under surface: few prickles. Color of upper surface: commonly near Yellow-Green Group 146B. Color of under surface: commonly near Yellow-Green Group 146B. Petiole length of terminal leaflet: commonly near 2.3 cm on average.

*Stipules*.—General appearance: adnate, pectinate and rather broad. Length: approximately 0.9 cm on average. Width: approximately 0.7 cm on average. Color of upper surface: commonly near Yellow-Green Group 146B. Color of under surface: commonly near Yellow-Green Group 146B.

Inflorescence:

*Number of flowers per stem*.—Generally between 1 and 12 flowers per stem.

*Inflorescence height*.—Approximately 9 cm on average when 2-12 flowers are present.

*Inflorescence width*.—Approximately 12 cm on average when 2-12 flowers are present.

*Pedicle*.—Length: approximately 2.5 cm on average. Diameter: approximately 0.2 cm on average. Texture: very slightly prickly. Color: commonly near Green Group 143C with few spots of near Greyed-Purple Group 185A.

*Bud*.—Shape: conical. Size: small. Length: approximately 1.9 cm on average. Width: approximately 1.7 cm on average. Color as calyx breaks: Upper surface: commonly near Red-Purple Group 57A amply suffused with near Red Group 53B. Under surface: commonly near Red-Purple Group 57A amply suffused with near Red Group 53B.

*Sepals*.—Length: approximately 2.0 cm on average. Width: approximately near 0.5 cm on average. Shape: with little extensions (approximately 0.5 cm on average). At the top: narrow and longish. At the base: flat to downward for open flowers. Upper surface: Texture: tomentous. Color: commonly near Yellow-Green Group 148C. Under surface: Texture: smooth. Color: commonly near Yellow-Green Group 146B.

*Receptacle*.—Color: commonly near Yellow-Green Group 146B. Length: approximately 0.7 cm on average. Width: approximately 0.5 cm on average. Surface: smooth. Shape: pitcher shaped.

*Peduncle*.—Length: approximately 3.5 to 4.0 cm on average. Width: approximately 0.3 cm on average. Surface: glandular. Color: commonly near Yellow-Green Group 146B.

*Flower*.—Average diameter when fully open: approximately 5 to 7 cm on average. Height: approximately 3 cm on average. Lastingness: approximately 1 week on average. Borne: commonly between 1 to 12 flowers per stem. Shape: cup shaped. Number of petals under normal conditions: approximately 12 to 15 petals on average. Shape of the petal: heart shape, medium petal incision. Base: obtuse. Top: rounded. Petal undulation: weak. Petal margin: not crenated. Texture of the petal: leathery. Petal length: approximately 3.1 cm on average. Petal width: approximately 2.7 cm on average. Petal arrangement: imbricated without petaloids. Petal drop: petals drop off cleanly before drying. Fragrance: none. Color when opening: Upper surface: commonly near Red-Purple Group 57A suffused with near Red Group 53B. Under surface: commonly between near Red-Purple Group 57A and near Red-Purple Group 57B. Color of the open flower: Upper surface: commonly near Red-Purple Group 57B; little spot at the base is commonly near Yellow Group 2D. Under surface: commonly near Red-Purple Group 57C; little spot at the base is near Yellow Group 2D. Color of the flower when fading: commonly near Red-Purple Group 57B. Anthers: number is approximately 71 on average, length is approximately 0.1 cm on average, coloration is commonly near Yellow-Orange Group 22C, and arrangement is regular around styles. Filaments: length is approximately 0.4 cm on average and coloration is commonly near Red Group 44D. Styles: length is approximately 0.3 cm on average, coloration is commonly near Red Group 44C, and number is approximately 49 on average. Stigmas: size is approximately 0.1 cm on average and coloration is commonly near Yellow Group 2C. Pollen: color is commonly near Greyed-Yellow Group 160A. Hips: not available at this stage.

Development:

*Vegetation*.—Very strong.

*Blooming*.—Very early in the season, very abundant and nearly continuous.

*Hardiness*.—USDA Zone 4 to 9.

*Tolerance to disease*.—Exceptional, and particularly against rust (*Phragmidium tuberculatum* and *Phragmidium mucronatum*) and Black Spot (*Diplocarpon rosae*).

The new 'MEICERAFYN' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Bedding Rose plant characterized by the following combination of characteristics:

(a) very abundantly and nearly continuously forms attractive, cup-shaped, red- purple colored blossoms, (b) forms attractive, very dense, glossy foliage, (c) exhibits exceptional tolerance to diseases, particularly against rust and Black Spot, (d) is very floriferous, (e) exhibits a compact, bushy growth habit, and (f) is well suited for providing attractive ornamentation; substantially as herein shown and described.

* * * * *

MEICERAFYN